(12) United States Patent
Wang

(10) Patent No.: US 6,812,373 B2
(45) Date of Patent: Nov. 2, 2004

(54) MODIFIED METALLOALUMINOPHOSPHATE MOLECULAR SIEVES

(75) Inventor: Kun Wang, Bridgewater, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 10/317,701

(22) Filed: Dec. 12, 2002

(65) Prior Publication Data

US 2004/0116761 A1 Jun. 17, 2004

(51) Int. Cl.[7] .............................. C07C 1/00; C07C 1/20; B01J 27/182
(52) U.S. Cl. ...................... 585/638; 585/639; 585/640; 502/208; 502/214
(58) Field of Search .............................. 502/208, 214; 585/638, 639, 640

(56) References Cited

U.S. PATENT DOCUMENTS

| | | | |
|---|---|---|---|
| 3,911,041 A | 10/1975 | Kaeding et al. | 260/682 |
| 3,979,472 A | 9/1976 | Butter | 260/668 |
| 4,088,706 A | 5/1978 | Kaeding | 260/668 |
| 4,159,282 A | 6/1979 | Olson et al. | |
| 4,414,005 A * | 11/1983 | De Bievre et al. | 95/127 |
| 4,471,150 A | 9/1984 | Wu | 585/640 |
| 4,752,596 A | 6/1988 | Bergna et al. | 502/64 |
| 5,145,816 A | 9/1992 | Beck et al. | 502/60 |
| 5,250,484 A | 10/1993 | Beck et al. | 502/71 |
| 5,981,418 A | 11/1999 | Drake et al. | 502/64 |
| 6,046,371 A | 4/2000 | Wu et al. | 585/638 |
| 6,080,901 A | 6/2000 | Drake et al. | 585/407 |
| 6,107,534 A | 8/2000 | Drake et al. | 585/411 |
| 6,114,268 A | 9/2000 | Wu et al. | 502/74 |
| 6,156,689 A | 12/2000 | Kimble et al. | 502/77 |
| 6,372,680 B1 | 4/2002 | Wu et al. | 502/64 |
| 6,472,569 B1 | 10/2002 | Wu et al. | 568/698 |

FOREIGN PATENT DOCUMENTS

| | | | |
|---|---|---|---|
| WO | WO 97/26989 | 7/1997 | B01J/29/04 |
| WO | WO 98/15496 | 4/1998 | C01B/25/45 |
| WO | WO 00/63144 | 10/2000 | C07C/41/09 |
| WO | WO 02/070407 | 9/2002 | C01B/37/08 |
| WO | WO 02/085514 | 10/2002 | B01J/29/00 |

OTHER PUBLICATIONS

Dahl, I. M. et al., *Catal. Lett.*, vol. 20, pp. 329–336 (1993).
Dahl, I. M. et al., *J. Catal.* vol. 149, pp. 458–464 (1994).
Dahl, I. M. et al., *J. Catal.* vol. 161, pp. 304–309 (1996).
Goguen, P.W. et al., *J. Am. Chem. Soc.*, vol. 120 pp. 2650–2651 (1998).
Song et al., *J. Am. Chem. Soc.*, vol. 122, pp. 10726–10727 (2000).
Song et al., *J. Am. Chem. Soc.*, vol. 123, pp. 4749–4754 (2001).
Song et al., *J. Phys. Chem.*, B, vol. 105, pp. 12839–12843 (2001).
Arstad, B. et al., *Catal. Lett.*, vol. 71, pp. 209–212 (2001).
Arstad, B., et al., *J. Am. Chem. Soc.*, vol. 123, pp. 8137–8138 (2001).
Komiya et al., *Sekyiyu Gakkaishi*, vol. 28 (3), pp. 257–263 (1985).
Geimar et al., *Fortschr. Miner.*, vol. 65(1), pp. 115–128 (1987).
Wilson, S. T., et al., *Microporous and Mesoporous Materials*, vol. 28, pp. 125–137 (1999).
Patent Abstract of Japan, vol. 013, No. 238 (C–603), Jun. 5, 1989 & JP 01 050827 A (Agency of Ind Science & Technology), Feb. 27, 1989.
A. Thijs, et al., "Purification of gases in H–mordenite modified with silane and diborane", *Journal of the Chemical Society*, Faraday Transactions 1, vol. 79, 1983, pp. 2821–2834.

* cited by examiner

*Primary Examiner*—Elizabeth D. Wood

(57) ABSTRACT

The invention is directed to a method for modifying a microporous metalloaluminophosphate molecular sieve, the method comprising the steps of a) introducing a metal hydride compound within the cages of said microporous molecular sieve, and b) reacting said metal hydride compound with the acid groups located in the cages of the molecular sieve, wherein the metal hydride compound is selected from the group consisting of hydrides of metals of Groups 1 and 2 of the Periodic Table, compounds of formula $M^1M^2H_4$ and mixtures thereof, $M^1$ being a metal belonging to Group 13 of the Periodic Table and $M^2$ being a metal belonging to Group 1 of the Periodic Table. The invention also relates to modified metalloaluminophosphate molecular sieves, to catalyst particles containing them and the use of the modified metalloaluminophosphate molecular sieves in catalytic processes.

22 Claims, No Drawings

MODIFIED METALLOALUMINOPHOSPHATE MOLECULAR SIEVES

FIELD OF INVENTION

The present invention relates to modified metalloaluminophosphate molecular sieves, preferably modified silicoaluminophosphate molecular sieves, as well as to methods of preparing these modified molecular sieves. The present invention also relates to the use of these modified molecular sieves in catalytic processes, such as processes for the conversion of oxygenated hydrocarbon feedstocks.

BACKGROUND OF THE INVENTION

Olefins, particularly light olefins, have been traditionally produced from petroleum feedstocks by either catalytic or steam cracking. Oxygenates, however, are becoming an alternative feedstock for making light olefins, particularly ethylene and propylene. Promising oxygenate feedstocks are alcohols, such as methanol and ethanol, dimethyl ether, methyl ethyl ether, diethyl ether, dimethyl carbonate, and methyl formate. Many of these oxygenates can be produced from a variety of sources including natural gas. Because of the relatively low-cost of these sources, alcohol, alcohol derivatives, and other oxygenates have promise as an economical source for light olefin production.

One way of producing olefins is by the conversion of methanol to olefins (MTO) catalyzed by a molecular sieve. Useful molecular sieves for converting methanol to olefin(s) are non-zeolitic molecular sieves, in particular metalloaluminophosphates such as the silicoaluminophosphates (SAPO's). For example, U.S. Pat. No. 4,499,327 to Kaiser, fully incorporated herein by reference, discloses making olefins from methanol using a variety of SAPO molecular sieve catalysts. The process can be carried out at a temperature between 300° C. and 500° C., a pressure between 0.1 atmosphere to 100 atmospheres, and a weight hourly space velocity (WHSV) of between 0.1 and 40 $hr^{-1}$. Crystalline aluminosilicate zeolites have also been reported as catalysts for converting methanol and/or dimethyl ether to olefin-containing hydrocarbon mixtures. For example, U.S. Pat. No. 3,911,041 discloses that methanol can be converted to C2–C4 olefins by contacting the methanol at a temperature of 300° C. to 700° C. with a crystalline aluminosilicate zeolite catalyst which has a Constraint Index of 1–12, such as ZSM-5, and which contains at least 0.78% by weight of phosphorus incorporated in the crystal structure of the zeolite.

Zeolitic aluminosilicate molecular sieves contain a three-dimensional microporous crystal framework structure of $[SiO_2]$ and $[AlO_2]$ corner sharing tetrahedral units. Metalloaluminophosphate (MeAPO) molecular sieves, often qualified as non-zeolitic molecular sieves, contain a three-dimensional microporous crystal framework structure of $[MO_2]$, $[AlO_2]$ and $[PO_2]$ corner sharing tetrahedral units. When M is silicon, the molecular sieves are referred to as silicoaluminophosphate (SAPO) molecular sieves. There are a wide variety of aluminosilicate and MeAPO molecular sieves known in the art. Of these the more important examples as catalysts for the conversion of oxygenates to olefins include ZSM-5, ZK-5, ZSM-11, ZSM-12, ZSM-34, ZSM-35, erionite, chabazite, offretite, silicalite and other similar materials, SAPO-5, SAPO-11, SAPO-17, SAPO-18, SAPO-34, SAPO-35, SAPO-41, SAPO-56 and other similar materials. SAPO molecular sieves having the CHA framework type and especially SAPO-34 are particularly important catalysts. Another important class of SAPO molecular sieves consists of mixed or intergrown phases of molecular sieves having the CHA and AEI framework types. Examples of such materials are disclosed in WO 98/15496, published 16 Apr. 1998, and in WO 02/070407, published Sep. 12, 2002, both herein fully incorporated by reference.

While the aforementioned molecular sieves exhibit good catalytic properties in the conversion of methanol to olefins, there remains a need to improve their catalytic performance in order to decrease their selectivity to undesired saturated hydrocarbons and to increase their selectivity to desired light olefins (ethylene and propylene).

Various methods have been reported for treating and/or modifying crystalline molecular sieves in order to improve their catalytic performances. U.S. Pat. No. 5,250,484 discloses a method for making a surface inactivated catalyst composition comprising acidic porous crystalline material, in particular ZSM-23, having active internal Broensted acid sites and containing surface inactivating material having boron to nitrogen bonds. The method involves contacting the surface of the molecular sieve with aqueous ammonia borane solution. The modified catalysts are described for use in olefin oligomerization processes.

U.S. Pat. No. 6,046,371 discloses silylated silicoaluminophosphate compositions prepared by contacting calcined SAPOs with a silylating agent, preferably tetraalkyl orthosilicates and poly(alkylaryl)siloxanes. The silylated silicoaluminophosphate compositions are described as giving increased light olefin yields and decreased coke production, when used as catalysts in the conversion of oxygenated hydrocarbons to olefins.

U.S. Pat. No. 6,472,569 discloses catalyst systems comprising a silicoaluminophosphate impregnated with a compound selected from the group consisting of phosphoric acid, boric acid, tributyltin acetate, and combinations of any two or more thereof. These catalyst systems are described as giving increased light olefin yields and decreased coke production, when used as catalysts in the conversion of oxygenated hydrocarbons and/or ethers.

PCT Application WO 02/085514-A2 discloses a process for modifying a microporous framework defined by nanocages, such as SAPO-18 or SAPO-34. The modified microporous framework comprises and an inorganic compound in at least one of the nanocages, wherein said inorganic compound is a product formed by a reaction of a second inorganic molecule that has a kinetic diameter smaller than the kinetic diameter of the inorganic compound. The second inorganic compound is selected from the group consisting of $PH_3$, $SiH_4$, $Si_2H_6$ and $B_2H_6$. The inorganic compound may be selected from the group consisting of phosphoric acid, boric acid, silica, a product of the hydrolysis of $PH_3$, a product of the hydrolysis of $SiH_4$, a product of the hydrolysis of $Si_2H_6$, a product of the hydrolysis of $B_2H_6$, a product of the oxidation of $PH_3$, a product of the oxidation of $SiH_4$, a product of the oxidation of $Si_2H_6$ and a product of the oxidation of $B_2H_6$. This document discloses more specifically a process for modifying H-SAPO-34 by treating H-SAPO-34 with $PH_3$ and methanol in a reactor at 250° C., followed by heating to 600° C. The method requires the presence of methanol to form $P(CH_3)_3$ and $P(CH_3)_4^+$ species in the SAPO-34 nanocages. According to this document, the modified H-SAPO-34 delivers higher ethylene selectivity than unmodified H-SAPO-34.

Despite the various molecular sieve modifications reported in the literature, there remains a need to find other methods for improving molecular sieve catalytic performances, in order to decrease the selectivity of these molecular sieves to undesired saturated hydrocarbons and to increase their selectivity to desired light olefins (ethylene and propylene), when used as catalysts in the conversion of oxygenated hydrocarbons.

SUMMARY OF THE INVENTION

The present invention provides a method for modifying a microporous metalloaluminophosphate molecular sieve, the method comprising the steps of a) introducing a metal hydride compound within the cages of said microporous molecular sieve, and b) reacting said metal hydride compound with the acid groups located in the cages of the molecular sieve, wherein the metal hydride compound is selected from the group consisting of hydrides of metals of Groups 1 and 2 of the Periodic Table, compounds of formula $M^1M^2H_4$ and mixtures thereof, $M^1$ being a metal belonging to Group 13 of the Periodic Table and $M^2$ being a metal belonging to Group 1 of the Periodic Table. Preferably, $M^1$ is aluminum, boron, or a mixture of aluminum and boron.

In a preferred embodiment, reacting the metal hydride with the molecular sieve acid groups takes place at a temperature of from room temperature to 150° C.

In another preferred embodiment, molecular sieve with a solution or a slurry of the metal hydride compound in an aprotic organic solvent, more preferably under conditions that avoid the presence of water and/or alcohols.

The preferred molecular sieves that are modified according to this method are small pore or medium metalloaluminophosphate molecular sieves, more preferably SAPO-34 or SAPO-56.

In yet another embodiment, the method for modifying the molecular sieve further comprises a step of c) restoring at least a portion of the acid groups located in the cages of the molecular sieve by submitting the molecular sieve to a thermal treatment, preferably at a temperature of from about 30° C. to about 400° C., more preferably at a temperature of from 50° C. to 150° C. In a separate preferred embodiment, thermal treatment takes place in the presence of water, an alcohol, such as methanol, ethanol or mixtures thereof, nitrous oxides, carbon monoxide, carbon dioxide, sources of ammonia, and mixtures thereof.

The invention also relates to a microcrystalline metalloaluminophosphate molecular sieve having acid sites within its intracrystalline cages bound with a metal compound, the metal compound being selected from the group consisting of hydrides of metals of Groups 1 and 2 of the Periodic Table, compounds of formula $M^1M^2H_4$ and mixtures thereof, $M^1$ being a metal belonging to Group 13 of the Periodic Table and $M^2$ being a metal belonging to Group 1 of the Periodic Table. Preferably, $M^1$ is aluminum, boron, or a mixture of aluminum and boron.

The present invention further relates to a method of making molecular sieve catalyst particles, the method comprising a) combining a microcrystalline metalloaluminophosphate molecular sieve having acid sites within its intracrystalline cages bound with a metal compound, the metal compound being selected from the group consisting of $M^1H_x$, $M^1M^2H_y$, $M^2$ and $M^3$-H wherein $M^1$ is a metal belonging to Group 13 of the Periodic Table; $M^2$ is a metal belonging to Group 1 of the Periodic Table; and $M^3$ is a metal belonging to Group 2 of the Periodic Table, x ranging from 1 to 2 and y ranging from 1 to 3, with at least one binder and optionally at least one matrix to form a catalyst preparation mixture; b) forming catalyst particles from the catalyst preparation mixture obtained at step a); c) submitting the catalyst particles to a thermal treatment at a temperature of from about 30° C. to about 700° C. Preferably, the thermal treatment step is carried out in the presence of water, an alcohol, such as methanol, ethanol or mixtures thereof, nitrous oxides, carbon monoxide, carbon dioxide, sources of ammonia, and mixtures thereof.

In yet another embodiment, the present invention relates to a process for making olefins from an oxygenate feedstock comprising the steps of a) providing a metalloaluminophosphate molecular sieve; b) introducing a metal hydride compound within the cages of said microporous molecular sieve; c) reacting said metal hydride compound with the acid groups located in the cages of the molecular sieve, wherein the metal hydride compound is selected from the group consisting of hydrides of metals of Groups 1 and 2 of the Periodic Table, compounds of formula $M^1M^2H_4$ and mixtures thereof, $M^1$ being a metal belonging to Group 13 of the Periodic Table and $M^2$ being a metal belonging to Group 1 of the Periodic Table. Preferably, $M^1$ is aluminum, boron, or a mixture of aluminum and boron; d) restoring at least a portion of the acid groups located in the cages of the molecular sieve by submitting the molecular sieve to a thermal treatment; e) contacting the molecular sieve obtained at step d) with the oxygenate feedstock; f) recovering an olefin product.

DETAILED DESCRIPTION OF THE INVENTION

Introduction.

Molecular sieve materials such as metalloaluminophosphate molecular sieves (MeAPOs) comprise a three-dimensional microporous crystal framework structure. After calcination, they possess a void volume consisting of channels and cages within their molecular framework. Recent studies by Kolboe et al. and by Haw et al. indicate that the catalytic conversion of methanol to olefins over SAPO-34 proceeds through a so-called "hydrocarbon pool" mechanism (Dahl, I. M., Kolboe, S., Catal. Lett., 1993, 20, 329–336; Dahl, I. M., Kolboe, S., J. Catal., 1994, 149, 458–464; Dahl, I. M., Kolboe, S., J. Catal., 1996, 161, 304–309; Goguen, P. W., Xu, T., Barich, D. H., Skloss, T. W., Song, W., Wang, Z., Nicholas, J. B., Haw, J. F., J. Am. Chem. Soc., 1998, 120, 2650–2651; Song, W., Haw, J. F., Nicholas, J. B., Heneghan, C. S., J. Am. Chem. Soc., 2000, 122, 10726–10727; Song, W., Haw, J. F., J. Am. Chem. Soc., 2001, 123, 4749–4754; Song, W., Fu, H., Haw, J. F., J. Phys. Chem. B, 2001, 105, 12839–12843; Arstad, B., Kolboe, S., Catal. Lett., 2001, 71, 209–212; Arstad, B., Kolboe, S., J. Am. Chem. Soc., 2001, 123, 8137–8138; PCT Application WO 02/085514). According to this mechanism, and without wishing to be bound to any theory, methylated aromatic compounds (methylated benzene and/or methylated naphthalene) form within the molecular sieve cages during the methanol to olefins conversion. The amount and type of methylated aromatic compounds present in the molecular sieve cages are dependent on the number of acid sites in the molecular sieve cages, as well as on the size and shape of the molecular sieve cages. The amount and type of aromatic compounds present in the cages is believed to influence product selectivity during the conversion of methanol to light olefins.

The present invention is directed toward a method of partially filling the void volume of a microporous molecular sieve with a Volume Modifier, while maintaining the acid sites within the channels and cages of the molecular sieve. After this modification, the molecular sieve possesses increased selectivity to desired products, such as ethylene and propylene, and lowered selectivity to undesired products, such as propane and saturated and unsaturated hydrocarbons having more than 3 carbon atoms, when used to catalyze the conversion of oxygenates. The present invention provides an important catalytic improvement, not only for molecular sieves already known for their good performances in the oxygenates-to-olefins conversion such as SAPO-34, but also for other molecular sieves.

The modified molecular sieves of the present invention are obtained by modifying crystalline molecular sieves that can have a wide range of chemical and physical characteristics. Molecular sieves have been well classified by the Structure Commission of the International Zeolite Association according to the rules of the IUPAC Commission on Zeolite Nomenclature. A framework-type describes the topology and connectivity of the tetrahedrally coordinated atoms constituting the framework, and makes an abstraction of the specific properties for those materials. Framework-type molecular sieves for which a structure has been established, are assigned a three letter code and are described in the *Atlas of Zeolite Framework Types*, 5th edition, Elsevier, London, England (2001), which is herein fully incorporated by reference.

Crystalline molecular sieve materials all have 3-dimensional, four-connected framework structure of corner-sharing $TO_4$ tetrahedra, where T is any tetrahedrally coordinated cation. These molecular sieves are typically described in terms of the size of the ring that defines a pore, where the size is based on the number of T atoms in the ring. Other framework-type characteristics include the arrangement of rings that form a cage, and when present, the dimension of channels, and the spaces between the cages. See van Bekkum, et al., *Introduction to Zeolite Science and Practice, Second Completely Revised and Expanded Edition*, Volume 137, pages 1–67, Elsevier Science, B. V., Amsterdam, Netherlands (2001). In a preferred embodiment, the molecular sieve is a metalloaluminophosphate molecular sieve, more preferably a silicoaluminophosphate molecular sieve, having 8-or 10-ring structures, most preferably having 8-rings and an average channel pore size less than about 5 Å, preferably in the range of from 3 Å to about 5 Å, more preferably from 3 Å to about 4.5 Å, and most preferably from 3.5 Å to about 4.2 Å.

Non-limiting examples of small pore molecular sieves are molecular sieves that have the framework types AEI, AFT, AFX APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO. Non-limiting examples of medium pore molecular sieves are molecular sieves that have the framework types AFO, AEL, EUO, HEU, FER, MEL, MFI, MTW, MTT, TON. Non-limiting examples of large pore molecular sieves are molecular sieves that have the framework types BEA, CFI, EMT, FAU, LTL, MWW. Other non-limiting examples of molecular sieves include ANA, CLO, DON, GIS, MER, MOR, and SOD. Non-limiting examples of the preferred molecular sieves, particularly for converting an oxygenate containing feedstock into olefin(s), include AEI, AFX, BEA, CHA and KFI. In a more preferred embodiment, the molecular sieve of the invention has a CHA, KFI or AFX topology, or a combination thereof, most preferably an AFX topology.

Non limiting examples of preferred molecular sieves of the invention include one or a combination of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, AlPO-5, AlPO-11, AlPO-18, AlPO-31, AlPO-34, AlPO-36, AlPO-37, AlPO-46, and metal containing molecular sieves thereof. The more preferred molecular sieves of the invention include one or a combination of SAPO-17, SAPO-34, SAPO-35, SAPO-44, SAPO-56, AlPO-18 and AlPO-34, even more preferably one or a combination of SAPO-34 and SAPO-56, and metal containing molecular sieves thereof.

Crystalline Molecular Sieve Synthesis

The crystalline molecular sieves that can be modified according to the present invention may be prepared by a wide range of methods, well known in the art. Generally, molecular sieves are synthesized by the hydrothermal crystallization of one or several of a source of aluminum, a source of phosphorous, a templating agent, and a source of metal, preferably silicon. Typically, a combination of the selected sources of aluminum and phosphorous, optionally with one or more templating agents and/or one or more sources of silicon and/or other metal, are placed in a sealed pressure vessel, optionally lined with an inert plastic such as polytetrafluoroethylene, and heated, at a crystallization pressure and crystallization temperature, until a crystalline material is formed, and then recovered by filtration, centrifugation and/or decanting. In a preferred embodiment, at least one templating agent and at least one source of metal, most preferably silicon, is used.

Non-limiting examples of silicon sources include silicates, fumed silica, for example, Aerosil-200 available from Degussa Inc., New York, N.Y., and CAB-O-SIL M-5, silicon compounds such as tetraalkyl orthosilicates, for example, tetramethyl orthosilicate (TMOS) and tetraethylorthosilicate (TEOS), colloidal silicas or aqueous suspensions thereof, for example Ludox-HS-40 sol available from E.I. du Pont de Nemours, Wilmington, Del., silicic acid, alkali-metal silicate, or any combination thereof. The preferred source of silicon is a silica sol.

Non-limiting examples of aluminum sources include aluminum-containing compositions such as aluminum alkoxides, for example aluminum isopropoxide, aluminum phosphate, aluminum hydroxide, sodium aluminate, pseudo-boehmite, gibbsite and aluminum trichloride, or any combinations thereof. A preferred source of aluminum is pseudo-boehmite, particularly when producing a silicoaluminophosphate molecular sieve.

Non-limiting examples of phosphorous sources, which may also include aluminum-containing phosphorous compositions, include phosphorous-containing, inorganic or organic, compositions such as phosphoric acid, organic phosphates such as triethyl phosphate, and crystalline or amorphous aluminophosphates such as $AlPO_4$, phosphorous salts, or combinations thereof. The preferred source of phosphorous is phosphoric acid, particularly when producing a silicoaluminophosphate.

Templating agents are generally compounds that contain elements of Group 15 of the Periodic Table of Elements, particularly nitrogen, phosphorus, arsenic and antimony, more preferably nitrogen or phosphorous, and most preferably nitrogen. Typical templating agents of Group 15 of the Periodic Table of elements also contain at least one alkyl or aryl group, preferably an alkyl or aryl group having from 1 to 10 carbon atoms, and more preferably from 1 to 8 carbon atoms. The preferred templating agents are nitrogen-containing compounds such as amines and quaternary ammonium compounds.

The quaternary ammonium compounds, in one embodiment, are represented by the general formula $R_4N^+$, where each R is hydrogen or a hydrocarbyl or substituted hydrocarbyl group, preferably an alkyl group or an aryl group having from 1 to 10 carbon atoms. In one embodiment, the templating agents include a combination of one or more quaternary ammonium compound(s) and one or more of a mono-, di-or tri-substituted amine.

Non-limiting examples of templating agents include tetraalkyl ammonium compounds including salts thereof such as tetramethyl ammonium compounds including salts thereof, tetraethyl ammonium compounds including salts thereof, tetrapropyl ammonium compounds including salts thereof, and tetrabutylammonium compounds including salts thereof, cyclohexylamine, morpholine, di-n-propylamine (DPA), tripropylamine, triethylamine (TEA), triethanolamine, piperidine, 2-methylpyridine, N,N-dimethylbenzylamine, N,N-diethylethanolamine, dicyclohexylamine, N,N-dimethylethanolamine, choline, N,N'-dimethylpiperazine, 1,4-diazabicyclo(2,2,2)octane, N',N',N,N-tetramethyl-(1,6)hexanediamine, N-methyldiethanolamine, N-methyl-ethanolamine, N-methyl piperidine, 3-methyl-piperidine, N-methylcyclohexylamine, 3-methylpyridine, 4-methyl-pyridine, quinuclidine, N,N'-dimethyl-1,4-diazabicyclo(2,2,2) octane ion; di-n-butylamine, neopentylamine, di-n-pentylamine, isopropylamine, t-butylamine, ethylenediamine, pyrrolidine, and 2-imidazolidone.

Generally, the synthesis mixture described above is sealed in a vessel and heated, preferably under autogenous pressure, to a temperature in the range of from about 80° C. to about 250° C., preferably from about 100° C. to about 250° C., more preferably from about 125° C. to about 225° C., even more preferably from about 150° C. to about 180° C.

In yet another embodiment, the crystallization temperature is increased gradually or stepwise during synthesis, preferably the crystallization temperature is maintained constant, for a period of time effective to form a crystalline product. The time required to form the crystalline product is typically from immediately up to several weeks, the duration of which is usually dependent on the temperature; the higher the temperature the shorter the duration. In one embodiment, the crystalline product is formed under heating from about 30 minutes to around 2 weeks, preferably from about 45 minutes to about 240 hours, and more preferably from about 1 hour to about 120 hours.

In one embodiment, the synthesis of a molecular sieve is aided by seeds from another or the same framework type molecular sieve.

The hydrothermal crystallization is carried out with or without agitation, for example stirring or tumbling. The stirring or agitation during the crystallization period may be continuous or intermittent, preferably continuous agitation. Typically, the crystalline molecular sieve product is formed, usually in a slurry state, and is recovered by any standard technique well known in the art, for example centrifugation or filtration. The isolated or separated crystalline product, in an embodiment, is washed, typically, using a liquid such as water, from one to many times. The washed crystalline product is then optionally dried, preferably in air.

Depending on the ratio and the type of ingredients used to prepare the molecular sieve, molecular sieves with high or low silicon (Si) to aluminum (Al) ratios can be obtained. The pH of a reaction mixture containing at a minimum a silicon-, aluminum-, and/or phosphorous-composition, and a templating agent, should be in the range of from 2 to 10.

In one preferred embodiment, when a templating agent is used in the synthesis of a molecular sieve, it is preferred that the templating agent is substantially, preferably completely, removed after crystallization by numerous well known techniques, for example, heat treatments such as calcination. Calcination involves contacting the molecular sieve containing the templating agent with a gas, preferably containing oxygen, at any desired concentration at an elevated temperature sufficient to either partially or completely decompose and oxidize the templating agent.

Treatment with Metal Hydride Compounds.

According to the present invention, the cage volume of a microporous molecular sieve is modified by a method comprising the steps of a) introducing a metal hydride compound within the cages of said microporous molecular sieve and b) reacting said metal hydride compound with the acid groups located in the cages of the molecular sieve. The metal hydride compound is selected from the group consisting of hydrides of metals of Groups 1 and 2 of the Periodic Table, compounds of formula $M^1M^2H_4$ and mixtures thereof, $M^1$ being a metal belonging to Group 13 of the Periodic Table and $M^2$ being a metal belonging to Group 1 of the Periodic Table [using the IUPAC numbering system described in the *CRC Handbook of Chemistry and Physics*, 78th Edition, CRC Press, Boca Raton, Fla. (1997)].

This treatment can be applied to various types of molecular sieves, including small pore, medium pore and large pore molecular sieves. An important feature of the present invention is that the metal hydride compound (hereinafter referred to as Treating Agent) must be able to penetrate within the cages of the molecular sieve. Before using the Treating Agent, it is thus preferred to submit the molecular sieve to a heat treatment or calcination in order to remove the compounds that may be present in the void volume of the molecular sieve. Typical calcination temperatures are in the range from about 400° C. to about 1,000° C., preferably from about 500° C. to about 800° C., and most preferably from about 550° C. to about 700° C. Calcination preferably takes place in an environment such as air, nitrogen, helium, flue gas (combustion product lean in oxygen), or any combination thereof.

Also, it is preferable to use a Treating Agent having a kinetic diameter no larger (equal to or smaller), preferably smaller than the pore opening size of the molecular sieve. In a preferred embodiment, the Treating Agent is incorporated within the cages of a metalloaluminophosphate molecular sieve, most preferably a small pore metalloaluminophosphate molecular sieve.

The metal hydride compound is preferably selected from the group consisting of LiH, NaH, KH, $CaH_2$, $LiAlH_4$, $NaAlH_4$, $KAlH_4$, $LiBH_4$, $NaBH_4$, $KBH_4$, and mixtures thereof, more preferably selected from the group consisting of $LiAlH_4$, $NaBH_4$.

The Treating Agent can be introduced within the void volume of the molecular sieve by various methods that involve contacting the molecular sieve with the Treating Agent. One method consists in placing the molecular sieve in a gas atmosphere containing the Treating Agent, optionally in the presence of a diluting inert gas. Another method consists in contacting a liquid Treating Agent or a solution or a slurry of the Treating Agent with the microporous molecular sieve under conditions allowing the Treating Agent to reach the channels and cages within the framework of the molecular sieve. Non-limiting examples of such conditions include incipient wetness, immersion in the liquid with or without stirring. The solvent is preferably an organic aprotic solvent such as, for example, acetonitrile, dimethyl ether, diethyl ether, tetrahydrofuran, dimethyl formamide, liquid hydrocarbons such as benzene, toluene, alkanes having from 5 to 20 carbon atoms, cycloalkanes having from 5 to 20 carbon atoms, and mixtures thereof. In a preferred embodiment, contacting the molecular sieve with the Treating Agent takes place under conditions that avoid the presence of protic substances, such as for example, water and/or alcohols. For this purpose, the equipment, molecular sieves and solvents are carefully cleaned, dried and purified before contacting the molecular sieve with the Treating Agent.

The treatment may be carried out within a wide range of temperatures, including temperatures below room temperature, at room temperature and temperatures above room temperature, depending on the physical and chemical properties of the molecular sieve and Treating Agent used. A convenient range of temperature is from room temperature up to 500° C., provided the Treating Agent is stable at the chosen temperature. For temperature sensitive Treating Agents, typical preferred temperatures range from room temperature to 150° C., more preferably from room temperature to 100° C.

Without being bound to any particular theory, the Treating Agent is believed to react within the void volume of the molecular sieve with the molecular sieve acid groups (OH groups) located in the cages of the molecular sieve. The reaction is accompanied by hydrogen release and results in binding of metal compounds to the molecular sieve framework, resulting in a first treated molecular sieve. The first treated molecular sieve thus has acid sites within its intracrystalline cages bound with a metal compound, the metal compound being selected from the group consisting of hydrides of metals of Groups 1 and 2 of the Periodic Table, compounds of formula $M^1M^2H_4$ and mixtures thereof, $M^1$ being a metal belonging to Group 13 of the Periodic Table and $M^2$ being a metal belonging to Group 1 of the Periodic Table. Preferably, $M^1$ is aluminum, boron, or a mixture of aluminum and boron. The first treated molecular sieve is then typically submitted to a thermal treatment, in order to remove residual treating material, and to restore at least a portion, preferably essentially all, of the molecular sieve OH groups present in the channels and cages of the molecular sieve. Optionally, this thermal treatment is performed in the presence of a chemical agent which helps restore the molecular sieve OH groups. Non-limiting examples of such agents include water, alcohols, such as methanol or ethanol, nitrous oxides, carbon monoxide, carbon dioxide, sources of ammonia, and mixtures thereof. In a preferred embodiment, the agent that helps restore the molecular sieve OH groups is water or methanol, more preferably, water, most preferably water in the vapor phase. Thermal treatment of the first treated molecular sieve is typically carried out at a temperature of from about 100° C. to about 700° C., preferably from 30° C. to 400° C., most preferably from 50° C. to 200° C. The duration of the thermal treatment can vary within wide limits, depending on the Treating Agent used or depending on whether a chemical agent is used to help restore the molecular sieve OH groups. Typical durations range from 10 minutes to 48 hours, preferably from 20 minutes to 24 hours, more preferably from 30 minutes to 16 hours.

In the embodiment in which thermal treatment is carried out in the presence of agent that helps restore the molecular sieve OH groups, the agent is preferably in the gas phase and thermal treatment is carried out at a temperature of from room temperature to 500° C., preferably of from 25° C. to 300° C., more preferably of from 50° C. to 200° C.

Thermal treatment may optionally be followed by a calcination step. Typical calcination temperatures are in the range from about 400° C. to about 1,000° C., preferably from about 500° C. to about 800° C., and most preferably from about 550° C. to about 700° C., preferably in a calcination environment such as air, steam, nitrogen, helium, flue gas (combustion product lean in oxygen), or any combination thereof. In an embodiment, thermal treatment and calcination can be carried out simultaneously, optionally in the presence of the agent that helps restore the molecular sieve OH groups.

After thermal treatment, optionally accompanied or followed by calcination, a second treated molecular sieve is obtained. This second treated molecular sieve has a compound containing at least one M-O group, preferably containing only M-O groups, and hereinafter referred to as "Volume Modifier", within its cages and/or channels. Preferably, the Volume Modifier is present in an amount sufficient to fill as much as possible of the void volume (channels and cages, preferably the cages) of the molecular sieve, without affecting the catalytic activity of the molecular sieve. The preferred weight and volume of Volume Modifier will vary within a wide range of possible limits, depending on the molecular sieve used, in particular its channel and cage volume size, the size and chemical nature of the Treating Agent and the desired catalytic performances. For example, in the case of SAPO-56, void volume reductions of up to about 50% lead to significant catalytic improvements.

In order to achieve the desired level of void volume reduction, the treatment sequence described above can be repeated as many times as necessary. Each treatment sequence will result in the formation of additional Volume Modifier within the void volume of the molecular sieve Typically, molecular sieves used in catalytic processes, especially on a commercial scale, are formulated into catalyst compositions. Formulation can occur at several stages of the molecular sieve treatment according to the present invention: before treatment, after formation of the first treated molecular sieve but before formation of the second treated molecular sieve (i.e. before the thermal treatment step) or after formation of the second treated molecular sieve (i.e. after the thermal treatment step). Catalyst formulation can thus be done either on the crystalline molecular sieve, on the first treated molecular sieve or on the second treated molecular sieve, herein collectively referred to as molecular sieve composition.

In all three embodiments, a catalyst composition is made or formulated by combining a molecular sieve composition, with a binder and/or a matrix material. These formulated catalyst compositions are then, formed into useful shape and sized particles by well-known techniques such as spray drying, pelletizing, extrusion, and the like.

There are many different binders that are useful in forming catalyst compositions according to the invention. Non-limiting examples of binders that are useful alone or in combination include various types of hydrated alumina, silicas, and/or other inorganic oxide sol. One preferred alumina containing sol is aluminum chlorhydrol. The inorganic oxide sol acts like glue binding the synthesized molecular sieves and other materials such as the matrix together, particularly after thermal treatment. Upon heating, the inorganic oxide sol, preferably having a low viscosity, is converted into an inorganic oxide matrix component. For example, an alumina sol will convert to an aluminum oxide matrix following heat treatment.

In a preferred embodiment, the molecular sieve composition is combined with one or more matrix material(s). Matrix materials are typically effective in reducing overall catalyst cost, act as thermal sinks assisting in shielding heat from the catalyst composition for example during regeneration, densifying the catalyst composition, and increasing catalyst strength such as crush strength and attrition resistance.

Non-limiting examples of matrix materials include one or more of: clays, rare earth metal oxides, non-active metal oxides including magnesia, thoria, beryllia, quartz, silica or sols, and mixtures thereof, for example silica-magnesia, silica-zirconia, silica-titania, silica-alumina and silica-alumina-thoria. Preferably, the matrix material is a clay.

Upon combining the molecular sieve composition and the matrix material, and/or binder, in a liquid to form a slurry, mixing, preferably rigorous mixing is needed to produce a substantially homogeneous mixture containing the molecular sieve composition. Non-limiting examples of suitable liquids include one or a combination of water, alcohol, ketones, aldehydes, and/or esters. The most preferred liquid is water.

In one embodiment, the slurry of the molecular sieve composition, binder and matrix material is mixed or milled to achieve a sufficiently uniform slurry of sub-particles of the molecular sieve catalyst composition that is then fed to a forming unit that produces the molecular sieve catalyst composition. In a preferred embodiment, the forming unit is a spray dryer. Typically, the forming unit is maintained at a temperature sufficient to remove most of the liquid from the slurry, and from the resulting molecular sieve catalyst composition. The resulting catalyst composition when formed in this way takes the form of micro spheres.

When a spray drier is used as the forming unit, typically, the slurry of the molecular sieve composition and matrix material, and optionally a binder, is co-fed to the spray drying volume with a drying gas with an average inlet temperature ranging from 200° C. to 550° C., and a combined outlet temperature ranging from 100° C. to about 225° C. In an embodiment, the average diameter of the spray dried formed catalyst composition is from about 40 $\mu$m to about 300 $\mu$m, preferably from about 50 $\mu$m to about 250 $\mu$m, more preferably from about 50 $\mu$m to about 200 $\mu$m, and most preferably from about 65 $\mu$m to about 90 $\mu$m.

Once the catalyst composition is formed in a substantially dry or dried state, to further harden and/or activate the formed catalyst composition, a heat treatment such as calcination, at an elevated temperature is usually performed. In the embodiment where formulation of the first treated molecular sieve is performed, this calcination treatment can replace or be part of the thermal treatment used to generate the compound having at least one M-O bond in the cages and/or channels of the molecular sieve. A conventional calcination environment to harden the catalyst particles is air that typically includes a small amount of water vapor. Typical calcination temperatures are in the range from about 400° C. to about 1,000° C., preferably from about 500° C. to about 800° C., and most preferably from about 550° C. to about 700° C., preferably in a calcination environment such as air, nitrogen, helium, flue gas (combustion product lean in oxygen), or any combination thereof.

In a preferred embodiment, the catalyst composition is heated in nitrogen at a temperature of from about 600° C. to about 700° C. Heating is carried out for a period of time typically from 30 minutes to 15 hours, preferably from 1 hour to about 10 hours, more preferably from about 1 hour to about 5 hours, and most preferably from about 2 hours to about 4 hours.

Catalytic Processes

The molecular sieve compositions and catalyst compositions described above are useful in a variety of processes including: cracking, of for example a naphtha feed to light olefin(s) or higher molecular weight (MW) hydrocarbons to lower MW hydrocarbons; hydrocracking, of for example heavy petroleum and/or cyclic feedstock; isomerization, of for example aromatics such as xylene, polymerization, of for example one or more olefin(s) to produce a polymer product; reforming; hydrogenation; dehydrogenation; dewaxing, of for example hydrocarbons to remove straight chain paraffins; absorption, of for example alkyl aromatic compounds for separating out isomers thereof; alkylation, of for example aromatic hydrocarbons such as benzene and alkyl benzene, optionally with propylene to produce cumeme or with long chain olefins; transalkylation, of for example a combination of aromatic and polyalkylaromatic hydrocarbons; dealkylation; hydrodecylization; disproportionation, of for example toluene to make benzene and paraxylene; oligomerization, of for example straight and branched chain olefin(s); and dehydrocyclization.

The preferred process of the invention is a process directed to the conversion of a feedstock comprising one or more oxygenates to one or more olefin(s).

In a preferred embodiment of the process of the invention, the feedstock contains one or more oxygenates, more specifically, one or more organic compound(s) containing at least one oxygen atom. In a more preferred embodiment, the feedstock contains methanol and/or dimethyl ether, and most preferably methanol.

The feedstock containing one or more oxygenates, is converted in the presence of a molecular sieve catalyst composition into olefin(s) having 2 to 6 carbons atoms, most preferably ethylene and/or propylene.

In one embodiment, the feedstock can contain one or more diluent(s), typically used to reduce the concentration of the feedstock, and generally non-reactive to the feedstock or molecular sieve catalyst composition. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred. The diluent is used either in a liquid or a vapor form, or a combination thereof. The diluent is either added directly to a feedstock entering into a reactor or added directly into a reactor, or added with a molecular sieve catalyst composition.

The process for converting one or more oxygenates to olefins, in the presence of a molecular sieve catalyst composition of the invention, is carried out in a reactor system, operated as a fixed bed process, a fluidized bed process (including a turbulent bed process), preferably a continuous fluidized bed process, and most preferably a continuous high velocity fluidized bed process. The processes of the invention can take place in a variety of catalytic reactors such as hybrid reactors that have a dense bed or fixed bed reaction zones and/or fast fluidized bed reaction zones coupled together, circulating fluidized bed reactors, riser reactors, and the like. Suitable reactor types are described in for example U.S. Pat. No. 4,076,796, U.S. Pat. No. 6,287,522 (dual riser), and *Fluidization Engineering*, D. Kunii and O. Levenspiel, Robert E. Krieger Publishing Company, New York, N.Y. 1977, which are all herein fully incorporated by reference. The preferred reactor type are riser reactors generally described in *Riser Reactor, Fluidization and Fluid-Particle Systems*, pages 48 to 59, F. A. Zenz and D. F. Othmo, Reinhold Publishing Corporation, New York, 1960, and U.S. Pat. No. 6,166,282 (fast-fluidized bed reactor), and U.S. patent application Ser. No. 09/564,613 filed May 4, 2000 (multiple riser reactor), which are all herein fully incorporated by reference.

In the preferred embodiment, a fluidized bed process or high velocity fluidized bed process includes a reactor system, a regeneration system and a recovery system.

The reactor system preferably is a fluid bed reactor system having a first reaction zone within one or more riser reactor(s) and a second reaction zone within at least one disengaging vessel, preferably comprising one or more cyclones. In one embodiment, the one or more riser reactor(s) and disengaging vessel is contained within a single reactor vessel. Fresh feedstock, preferably containing one or more oxygenates, optionally with one or more diluent(s), is fed to the one or more riser reactor(s) in which a molecular sieve catalyst composition or coked version thereof is introduced. In one embodiment, the molecular sieve catalyst composition or coked version thereof is contacted with a liquid or gas, or combination thereof, prior to being introduced to the riser reactor(s), preferably the liquid is water or methanol, and the gas is an inert gas such as nitrogen.

In an embodiment, the amount of fresh feedstock fed separately or jointly with a vapor feedstock, to a reactor system is in the range of from 0.1 weight percent to about 85 weight percent, preferably from about 1 weight percent to about 75 weight percent, more preferably from about 5 weight percent to about 65 weight percent based on the total weight of the feedstock including any diluent contained therein. The liquid and vapor feedstocks are preferably the same composition, or contain varying proportions of the same or different feedstock with the same or different diluent.

The feedstock entering the reactor system is preferably converted, partially or fully, in the first reactor zone into a gaseous effluent that enters the disengaging vessel along with a coked molecular sieve catalyst composition. In the preferred embodiment, cyclone(s) within the disengaging vessel are designed to separate the molecular sieve catalyst composition, preferably a coked molecular sieve catalyst composition, from the gaseous effluent containing one or more olefin(s) within the disengaging zone. Cyclones are preferred, however, gravity effects within the disengaging vessel will also separate the catalyst compositions from the gaseous effluent. Other methods for separating the catalyst compositions from the gaseous effluent include the use of plates, caps, elbows, and the like.

In one embodiment of the disengaging system, the disengaging system includes a disengaging vessel, typically a lower portion of the disengaging vessel is a stripping zone. In the stripping zone the coked molecular sieve catalyst composition is contacted with a gas, preferably one or a combination of steam, methane, carbon dioxide, carbon monoxide, hydrogen, or an inert gas such as argon, preferably steam, to recover adsorbed hydrocarbons from the coked molecular sieve catalyst composition that is then introduced to the regeneration system.

The conversion temperature employed in the conversion process, specifically within the reactor system, is in the range of from about 200° C. to about 1000° C., preferably from about 250° C. to about 800° C., more preferably from about 250° C. to about 750° C., yet more preferably from about 300° C. to about 650° C., yet even more preferably from about 350° C. to about 600° C. most preferably from about 350° C. to about 550° C.

The conversion pressure employed in the conversion process, specifically within the reactor system, varies over a wide range including autogenous pressure. The conversion pressure is based on the partial pressure of the feedstock exclusive of any diluent therein. Typically the conversion pressure employed in the process is in the range of from about 0.1 kPaa to about 5 MPaa, preferably from about 5 kPaa to about 1 MPaa, and most preferably from about 20 kpaa to about 500 kPaa.

The weight hourly space velocity (WHSV), particularly in a process for converting a feedstock containing one or more oxygenates in the presence of a molecular sieve catalyst composition within a reaction zone, is defined as the total weight of the feedstock excluding any diluents to the reaction zone per hour per weight of molecular sieve in the molecular sieve catalyst composition in the reaction zone. The WHSV is maintained at a level sufficient to keep the catalyst composition in a fluidized state within a reactor. Typically, the WHSV ranges from about 1 $hr^{-1}$ to about 5000 $hr^{-1}$, preferably from about 2 $hr^{-1}$ to about 3000 $hr^{-1}$, more preferably from about 5 $hr^{-1}$ to about 1500 $hr^{-1}$, and most preferably from about 10 $hr^{-1}$ to about 1000 $hr^{-1}$. In one preferred embodiment, the WHSV is greater than 20 $hr^{-1}$, preferably the WHSV for conversion of a feedstock containing methanol and dimethyl ether is in the range of from about 20 $hr^{-1}$ to about 300 $hr^{-1}$.

The superficial gas velocity (SGV) of the feedstock including diluent and reaction products within the reactor system is preferably sufficient to fluidize the molecular sieve catalyst composition within a reaction zone in the reactor. The SGV in the process, particularly within the reactor system, more particularly within the riser reactor(s), is at least 0.1 meter per second (m/sec), preferably greater than 0.5 m/sec, more preferably greater than 1 m/sec, even more preferably greater than 2 m/sec, yet even more preferably greater than 3 m/sec, and most preferably greater than 4 m/sec.

The coked (used) molecular sieve catalyst composition is withdrawn from the disengaging vessel and introduced to the regeneration system. The regeneration system comprises a regenerator where the coked catalyst composition is contacted with a regeneration medium, preferably a gas containing oxygen, under general regeneration conditions of temperature, pressure and residence time. The regeneration temperature is in the range of from about 200° C. to about 1500° C., preferably from about 300° C. to about 1000° C., more preferably from about 450° C. to about 750° C., and most preferably from about 550° C. to about 700° C. The regeneration pressure is in the range of from about 15 psia (103 kPaa) to about 500 psia (3448 kPaa), preferably from about 20 psia (138 kPaa) to about 250 psia (1724 kPaa), more preferably from about 25 psia (172 kPaa) to about 150 psia (1034 kPaa), and most preferably from about 30 psia (207 kPaa) to about 60 psia (414 kPaa).

In an embodiment, a portion of the molecular sieve catalyst composition from the regenerator is returned directly to the one or more riser reactor(s), or indirectly, by pre-contacting with the feedstock, or contacting with fresh molecular sieve catalyst composition, or contacting with a regenerated molecular sieve catalyst composition or a cooled regenerated molecular sieve catalyst composition described below.

The burning of coke is an exothermic reaction, and in an embodiment, the temperature within the regeneration system is controlled by various techniques in the art including feeding a cooled gas to the regenerator vessel, operated either in a batch, continuous, or semi-continuous mode, or a combination thereof. A preferred technique involves withdrawing the regenerated molecular sieve catalyst composition from the regeneration system and passing the regenerated molecular sieve catalyst composition through a catalyst cooler that forms a cooled regenerated molecular sieve catalyst composition. The catalyst cooler, in an embodiment, is a heat exchanger that is located either internal or external to the regeneration system. Other methods for operating a regeneration system are in disclosed U.S. Pat. No. 6,290,916 (controlling moisture), which is herein fully incorporated by reference.

The regenerated molecular sieve catalyst composition withdrawn from the regeneration system, preferably from the catalyst cooler, is combined with a fresh molecular sieve catalyst composition and/or re-circulated molecular sieve catalyst composition and/or feedstock and/or fresh gas or liquids, and returned to the riser reactor(s). In another embodiment, the regenerated molecular sieve catalyst composition withdrawn from the regeneration system is returned to the riser reactor(s) directly, preferably after passing through a catalyst cooler. In one embodiment, a carrier, such as an inert gas, feedstock vapor, steam or the like, semi-continuously or continuously, facilitates the introduction of the regenerated molecular sieve catalyst composition to the reactor system, preferably to the one or more riser reactor(s).

By controlling the flow of the regenerated molecular sieve catalyst composition or cooled regenerated molecular sieve catalyst composition from the regeneration system to the reactor system, the optimum level of coke on the molecular sieve catalyst composition entering the reactor is maintained. There are many techniques for controlling the flow of a molecular sieve catalyst composition described in Michael Louge, *Experimental Techniques, Circulating Fluidized Beds*, Grace, Avidan and Knowlton, eds., Blackie, 1997 (336–337), which is herein incorporated by reference.

Coke levels on the molecular sieve catalyst composition are measured by withdrawing from the conversion process the molecular sieve catalyst composition at a point in the process and determining its carbon content. Typical levels of coke on the molecular sieve catalyst composition, after regeneration is in the range of from 0.01 weight percent to about 15 weight percent, preferably from about 0.1 weight percent to about 10 weight percent, more preferably from about 0.2 weight percent to about 5 weight percent, and most preferably from about 0.3 weight percent to about 2 weight percent based on the total weight of the molecular sieve and not the total weight of the molecular sieve catalyst composition.

The gaseous effluent is withdrawn from the disengaging system and is passed through a recovery system. There are many well known recovery systems, techniques and sequences that are useful in separating olefin(s) and purifying olefin(s) from the gaseous effluent. Recovery systems generally comprise one or more or a combination of a various separation, fractionation and/or distillation towers, columns, splitters, or trains, reaction systems such as ethylbenzene manufacture (U.S. Pat. No. 5,476,978) and other derivative processes such as aldehydes, ketones and ester manufacture (U.S. Pat. No. 5,675,041), and other associated equipment for example various condensers, heat exchangers, refrigeration systems or chill trains, compressors, knock-out drums or pots, pumps, and the like.

Non-limiting examples of these towers, columns, splitters or trains used alone or in combination include one or more of a de-methanizer, preferably a high temperature de-methanizer, a de-ethanizer, a de-propanizer, a wash tower often referred to as a caustic wash tower and/or quench tower, absorbers, adsorbers, membranes, ethylene (C2) splitter, propylene (C3) splitter, butene (C4) splitter, and the like.

Various recovery systems useful for recovering predominately olefin(s), preferably prime or light olefin(s) such as ethylene, propylene and/or butene are described in U.S. Pat. No. 5,960,643 (secondary rich ethylene stream), U.S. Pat. Nos. 5,019,143, 5,452,581 and 5,082,481 (membrane separations), U.S. Pat. No. 5,672,197 (pressure dependent adsorbents), U.S. Pat. No. 6,069,288 (hydrogen removal), U.S. Pat. No. 5,904,880 (recovered methanol to hydrogen and carbon dioxide in one step), U.S. Pat. No. 5,927,063 (recovered methanol to gas turbine power plant), and U.S. Pat. No. 6,121,504 (direct product quench), U.S. Pat. No. 6,121,503 (high purity olefins without superfractionation), and U.S. Pat. No. 6,293,998 (pressure swing adsorption), which are all herein fully incorporated by reference.

Generally accompanying most recovery systems is the production, generation or accumulation of additional products, by-products and/or contaminants along with the preferred prime products. The preferred prime products, the light olefins, such as ethylene and propylene, are typically purified for use in derivative manufacturing processes such as polymerization processes. Therefore, in the most preferred embodiment of the recovery system, the recovery system also includes a purification system. For example, the light olefin(s) produced particularly in a methanol-to-olefins process are passed through a purification system that removes low levels of by-products or contaminants.

Non-limiting examples of contaminants and by-products include generally polar compounds such as water, alcohols, carboxylic acids, ethers, carbon oxides, sulfur compounds such as hydrogen sulfide, carbonyl sulfides and mercaptans, ammonia and other nitrogen compounds, arsine, phosphine and chlorides. Other contaminants or by-products include hydrogen and hydrocarbons such as acetylene, methyl acetylene, propadiene, butadiene and butyne.

Other recovery systems that include purification systems, for example for the purification of olefin(s), are described in *Kirk-Othmer Encyclopedia of Chemical Technology*, 4th Edition, Volume 9, John Wiley & Sons, 1996, pages 249–271 and 894–899, which is herein incorporated by reference. Purification systems are also described in for example, U.S. Pat. No. 6,271,428 (purification of a diolefin hydrocarbon stream), U.S. Pat. No. 6,293,999 (separating propylene from propane), and U.S. patent application Ser. No. 09/689,363 filed Oct. 20, 2000 (purge stream using hydrating catalyst), which is herein incorporated by reference.

Typically, in converting one or more oxygenates to olefin(s) having 2 or 3 carbon atoms, an amount of hydrocarbons, particularly olefin(s), especially olefin(s) having 4 or more carbon atoms, and other by-products are formed or produced. Included in the recovery systems of the invention are reaction systems for converting the products contained within the effluent gas withdrawn from the reactor or converting those products produced as a result of the recovery system utilized.

In an embodiment, an integrated process is directed to producing light olefin(s) from a hydrocarbon feedstock, preferably a hydrocarbon gas feedstock, more preferably methane and/or ethane. The first step in the process is passing the gaseous feedstock, preferably in combination with a water stream, to a syngas production zone to produce a synthesis gas (syngas) stream. Syngas production is well known, and typical syngas temperatures are in the range of from about 700° C. to about 1200° C. and syngas pressures are in the range of from about 2 MPa to about 100 MPa. Synthesis gas streams are produced from natural gas, petroleum liquids, and carbonaceous materials such as coal, recycled plastic, municipal waste or any other organic material, preferably synthesis gas stream is produced via steam reforming of natural gas.

Generally, a heterogeneous catalyst, typically a copper based catalyst, is contacted with a synthesis gas stream, typically carbon dioxide and carbon monoxide and hydrogen to produce an alcohol, preferably methanol, often in combination with water. In one embodiment, the synthesis gas stream at a synthesis temperature in the range of from about 150° C. to about 450° C. and at a synthesis pressure in the range of from about 5 MPa to about 10 MPa is passed through a carbon oxide conversion zone to produce an oxygenate containing stream.

This oxygenate containing stream, or crude methanol, typically contains the alcohol product and various other components such as ethers, particularly dimethyl ether, ketones, aldehydes, dissolved gases such as hydrogen methane, carbon oxide and nitrogen, and fuel oil. The oxygenate containing stream, crude methanol, in the preferred embodiment is passed through a well known purification processes, distillation, separation and fractionation, resulting in a purified oxygenate containing stream, for example, commercial Grade A and AA methanol.

The oxygenate containing stream or purified oxygenate containing stream, optionally with one or more diluents, is contacted with one or more molecular sieve catalyst composition described above in any one of the processes described above to produce a variety of prime products, particularly light olefin(s), ethylene and/or propylene. Non-limiting examples of this integrated process are described in EP-B-0 933 345, which is herein fully incorporated by reference.

In another more fully integrated process, optionally with the integrated processes described above, olefin(s) produced are directed to, in one embodiment, one or more polymerization processes for producing various polyolefins. (See for example U.S. patent application Ser. No. 09/615,376 filed Jul. 13, 2000, which is herein fully incorporated by reference.)

Polymerization processes include solution, gas phase, slurry phase and a high pressure processes, or a combination thereof. Particularly preferred is a gas phase or a slurry phase polymerization of one or more olefin(s) at least one of which is ethylene or propylene.

These polymerization processes utilize a polymerization catalyst that can include any one or a combination of the molecular sieve catalysts discussed above, however, the preferred polymerization catalysts are those Ziegler-Natta, Phillips-type, metallocene, metallocene-type and advanced polymerization catalysts, and mixtures thereof.

In preferred embodiment, the integrated process comprises a polymerizing process of one or more olefin(s) in the presence of a polymerization catalyst system in a polymerization reactor to produce one or more polymer products, wherein the one or more olefin(s) having been made by converting an alcohol, particularly methanol, using a molecular sieve catalyst composition. The preferred polymerization process is a gas phase polymerization process and at least one of the olefins(s) is either ethylene or propylene, and preferably the polymerization catalyst system is a supported metallocene catalyst system. In this embodiment, the supported metallocene catalyst system comprises a support, a metallocene or metallocene-type compound and an activator, preferably the activator is a non-coordinating anion or alumoxane, or combination thereof, and most preferably the activator is alumoxane.

The polymers produced by the polymerization processes described above include linear low density polyethylene, elastomers, plastomers, high density polyethylene, low density polyethylene, polypropylene and polypropylene copolymers. The propylene based polymers produced by the polymerization processes include atactic polypropylene, isotactic polypropylene, syndiotactic polypropylene, and propylene random, block or impact copolymers.

EXAMPLES

In order to provide a better understanding of the present invention including representative advantages thereof, the following examples are offered. In these examples, X-ray Diffractograms were recorded on a Philips PW 1840 powder diffractometer, using Ni-filtered Cu Kα radiation (X=0.154 nm).

Example 1
Microcrystalline Molecular Sieve.

SAPO-34 was prepared according to the following procedure. The following ingredients were mixed, in sequence, into a uniform gel: pseudoboehmite alumina (Condea Pural SB-F) and $H_2O$, a solution of 85 wt % semi-conductor grade phosphoric acid and $H_2O$, colloidal silica (40%, Nalco), tetraethylammoniumhydroxide (35%, Sachem) and dipropylamine. The molar ratio of the ingredients was:

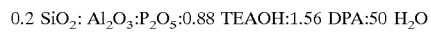

$0.2\ SiO_2: Al_2O_3:P_2O_5:0.88\ TEAOH:1.56\ DPA:50\ H_2O$

The synthesis mixture was placed in an stainless steel autoclave, stirred and heated to 170° C. for 35 hrs. The solid product was washed with deionized water and dried. The solid product yield was 11%. XRD pattern shows that the product is SAPO-34.

Example 2
Treatment of SAPO-34 with $LiAlH_4$ or $NaBH_4$.

As synthesized SAPO-34 was calcined at 650° C. for 10 hours. An amount of 3.0 g of calcined SAPO-34 was placed in a 100-ml round bottom flask. The flask was evacuated under vacuum and 30 ml of anhydrous tetrahydrofuran (THF, Aldrich) was cannulated into the flask. The mixture was allowed to stir for 30 minutes and 2.0 mL of a 1.0 M solution of lithium aluminium hydride in THF (available from Aldrich) was then slowly added via a gas-tight syringe. Gas evolution was observed upon addition of the hydride solution. The atomic ratio of aluminum added to silicon in the molecular sieve was 0.5. The mixture was stirred for 18 hours, separated by centrifuge and washed with 30 mL of THF. The solid obtained was then stirred in 30 mL of methanol for 12 hours, separated and dried in an oven at 105° C. for 12 hours.

b) The procedure described in a) above was repeated, except 4.0 mL of the 1.0 M lithium aluminium hydride solution was used.

c) SAPO-34 was calcined at 650° C. for 10 hours. An amount of 3.0 g of calcined SAPO-34 was placed in a 100-ml round bottom flask. The flask was evacuated under vacuum and 40 ml of anhydrous dimethylformamide (DMF, Aldrich) was cannulated into the flask. The mixture was allowed to stir for 30 minutes. Separately, an amount of 78 mg of sodium borohydride (Aldrich) was dissolved in 5.0 mL of anhydrous DMF under nitrogen and the solution was added slowly via a gas-tight syringe to the flask containing SAPO-34. Gas evolution was observed upon addition of the hydride solution. The atomic ratio of boron added to silicon in the molecular sieve was 0.5. The mixture was stirred for 24 hours, separated by centrifuge and washed twice with 30 mL of methanol. The solid obtained was dried in an oven at 105° C. for 12 hours.

d) The procedure described in c) above was repeated, except 155 mg of sodium borohydride dissolved in 5.0 mL of anhydrous DMF was used.

While the present invention has been described and illustrated by reference to particular embodiments, those of ordinary skill in the art will appreciate that the invention lends itself to variations not necessarily illustrated herein. For example, it is also contemplated the molecular sieves described herein are useful as absorbents, adsorbents, gas separators, detergents, water purifiers, and in other various uses in various areas such as agriculture and horticulture.

What is claimed is:

1. A method for modifying a microporous metalloaluminophosphate molecular sieve, the method comprising the steps of
   a) introducing a metal hydride compound within the cages of said microporous molecular sieve and
   b) reacting said metal hydride compound with the acid groups located in the cages of the molecular sieve,
wherein the metal hydride compound is selected from the group consisting of hydrides of metals of Groups 1 and 2 of the Periodic Table, compounds of formula $M^1M^2H_4$ and mixtures thereof, $M^1$ being a metal belonging to Group 13 of the Periodic Table and $M^2$ being a metal belonging to Group 1 of the Periodic Table.

2. The method of claim 1, wherein $M^1$ is aluminum, boron, or a mixture of aluminum and boron.

3. The method of claim 1, wherein the metal hydride compound is selected from the group consisting of LiH, NaH, KH, $CaH_2$, $LiAlH_4$, $NaAlH_4$, $KAlH_4$, $LiBH_4$, $NaBH_4$, $KBH_4$ and mixtures thereof.

4. The method of claim 1, wherein reacting the metal hydride with the molecular sieve acid groups takes place at a temperature of from room temperature to 150° C.

5. The method of claim 1, wherein introducing the metal hydride compound within the cages of the microporous molecular sieve takes place by contacting the molecular sieve with a solution or a slurry of the metal hydride compound in an aprotic organic solvent.

6. The method of claim 5, wherein contacting the molecular sieve with a solution or a slurry of the metal hydride compound takes place under conditions that avoid the presence of water and/or alcohols.

7. The method of claim 1, wherein the molecular sieve is a small pore or medium pore metalloaluminophosphate molecular sieve.

8. The method of claim 1, wherein the molecular sieve is SAPO-34 or SAPO-56.

9. The method of claim 1, further comprising the step of c) restoring at least a portion of the acid groups located in the cages of the molecular sieve by submitting the molecular sieve to a thermal treatment.

10. The method of claim 9, wherein thermal treatment takes place at a temperature of from about 30° C. to about 400° C.

11. The method of claim 9, wherein thermal treatment takes place at a temperature of from 50° C. to 150° C.

12. The method of claim 9, wherein thermal treatment takes place in the presence of a compound selected from the group consisting or water, an alcohol, nitrous oxides, carbon monoxide, carbon dioxide, sources of ammonia, and mixtures thereof.

13. The method of claim 9, wherein thermal treatment is followed by a calcination step.

14. A microcrystalline metalloaluminophosphate molecular sieve having acid sites within its intracrystalline cages bound with a metal compound, the metal compound being selected from the group consisting of hydrides of metals of Groups 1 and 2 of the Periodic Table, compounds of formula $M^1M^2H_4$ and mixtures thereof, $M^1$ being a metal belonging to Group 13 of the Periodic Table and $M^2$ being a metal belonging to Group 1 of the Periodic Table.

15. The microcrystalline molecular sieve of claim 14, wherein the metal compound is compounds of the formula $M^1M^2H_4$ and mixtures thereof, $M^1$ being a metal belonging to Group 13 of the Periodic Table and $M^2$ being a metal belonging to Group 1 of the Periodic Table.

16. The molecular sieve of claim 15, wherein the molecular sieve has the AFX or CHA framework type.

17. A method of making molecular sieve catalyst particles, the method comprising
   a) combining a microcrystalline metalloaluminophosphate molecular sieve having acid sites within its intracrystalline cages bound with a metal compound, the metal compound being selected from the group consisting of hydrides of metals of Groups 1 and 2 of the Periodic Table, compounds of formula $M^1M^2H_4$ and mixtures thereof, $M^1$ being a metal belonging to Group 13 of the Periodic Table and $M^2$ being a metal belonging to Group 1 of the Periodic Table, with at least one binder and optionally at least one matrix to form a catalyst preparation mixture;
   b) forming catalyst particles from the catalyst preparation mixture obtained at step a);
   c) submitting the catalyst particles to a thermal treatment at a temperature of from about 30° C. to about 700° C.

18. The method of claim 17, wherein thermal treatment takes place in the presence of a compound selected from the group consisting of water, an alcohol nitrous oxides, carbon monoxide, carbon dioxide, sources of ammonia, and mixtures thereof.

19. The method of claim 17, wherein the binder is alumina.

20. The method of claim 17, wherein the matrix is a clay.

21. The method of claim 17, wherein forming catalyst particles from the catalyst preparation mixture is performed by spray drying said catalyst preparation mixture.

22. A process for making olefins from an oxygenate feedstock comprising the steps of a) providing a metalloaluminophosphate molecular sieve; b) introducing a metal hydride compound within the cages of said microporous molecular sieve; c) reacting said metal hydride compound with the acid groups located in the cages of the molecular sieve, wherein the metal hydride compound is selected from the group consisting of hydrides of metals of Groups 1 and 2 of the Periodic Table, compounds of formula $M^1M^2H_4$ and mixtures thereof, $M^1$ being a metal belonging to Group 13 of the Periodic Table and $M^2$ being a metal belonging to Group 1 of the Periodic Table; d) restoring at least a portion of the acid groups located in the cages of the molecular sieve by submitting the molecular sieve to a thermal treatment; e) contacting the molecular sieve obtained at step d) with the oxygenate feedstock; f) recovering an olefin product.

* * * * *